United States Patent [19]

Solli et al.

[11] 4,002,615

[45] Jan. 11, 1977

[54] TERPENOID COMPOUNDS OF SUBSTITUTED HYDROXYALKYL-PYRIDINES HAVING JUVENILE HORMONE ACTIVITY

[75] Inventors: Hauk Solli, Harboor; Per Dausell Klemmensen, Lemvig; Preben Lindholm Holst, Harboor; Hans Berg Madsen, Bovlingbjerg, all of Denmark

[73] Assignee: A/S Cheminova, Lemvig, Denmark

[22] Filed: July 25, 1974

[21] Appl. No.: 491,970

[30] Foreign Application Priority Data

Mar. 13, 1974 United Kingdom ............ 11201/74

[52] U.S. Cl. .................... 260/240 H; 424/263; 260/295 R; 260/295.5 R; 260/297 R; 260/348 R; 260/348.5 R; 260/614 A; 260/614 R
[51] Int. Cl.² ...................................... C07D 405/12
[58] Field of Search ....... 260/240 H, 297 R, 295 R, 260/295.5 R

[56] References Cited

UNITED STATES PATENTS

| | | |
|---|---|---|
| 3,686,222 | 8/1972 | Chodnekar et al. ............ 260/340.5 |
| 3,823,162 | 7/1974 | Wah Wat ........................ 260/340.7 |
| 3,864,334 | 2/1975 | Pallos ........................ 260/297 R X |
| 3,867,543 | 2/1975 | Kohn ........................ 260/297 R X |
| 3,941,777 | 3/1976 | Madsen et al. ................ 260/240 H |

*Primary Examiner* — John D. Randolph
*Attorney, Agent, or Firm* — Beveridge, DeGrandi, Kline & Lunsford

[57] ABSTRACT

This invention is concerned with certain terpenoid compounds of substituted hydroxy-alkylpyridines, and their preparation and use. These compounds possess improved juvenile hormonal activity which can be utilized first and foremost to inhibit the metamorphosis of insect larvae and to act as sterilizing or ovicidal agent and, consequently, can be utilized in the control of insects.

9 Claims, No Drawings

TERPENOID COMPOUNDS OF SUBSTITUTED HYDROXYALKYL-PYRIDINES HAVING JUVENILE HORMONE ACTIVITY

This invention is for improvements in or relating to compounds having juvenile hormone activity. More particularly, the present invention relates to novel terpenoid compounds of substituted hydroxy-alkylpyridines, and to the methods and compositions for the control of insects by means of these novel compounds.

A number of substances are known to have juvenile hormone activity demonstrated by retention of larval and pupal characters, inhibition of metamorphosis and stimulation of ovarian growth in adult females together with ovicidal activity. Such substances are generally known as Insect Growth Regulaters (IGR). For a comprehensive review see Slama, Romanuk and Sorm; Insect Hormones and Bioanalogues; Springer Verlag; Wienna 1974.

It is known from the literature that compounds with a terpenoid chain attached to various functional groups show juvenile hormone activity. Schwartz, M. et al.: Science, 167, 191–2 (1970), Journ. Econ. Ent., 63, 1858–60, (1970), Belgian Pat. No. 734904, Danish Pat. No. 127668 and West German OLS No. 2247399.

Some of these compounds exhibit high activity when applied topically to the insect, influence its development and prevent formation of sexually mature adults.

The compounds of the present invention act selectively on certain insects and, moreover, exhibit strong sterilizing properties. The compounds, the preparation and application of which is described herein, represent novel analogues of the insect juvenile hormone which are cheaper and easier to prepare than many known analogues.

The novel compounds of the present invention are compounds represented by the following general formula (I)

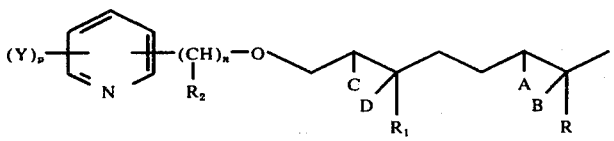

(I)

wherein the symbols are as follows:
 A: a hydrogen atom,
 B: a hydrogen atom, an alkyl group or an alkoxy group, or,
 A B: when taken together, a further single bond between the adjacent carbon atoms, or an oxygen atom,
 C: a hydrogen atom,
 D: a hydrogen atom, or,
 C D: when taken together, a further single bond between the adjacent carbon atoms,
 R: a methyl or an ethyl group,
 $R_1$: a methyl or an ethyl group,
 $n$: an integer from 1 to 3,
 $R_2$: an alkyl group or a hydrogen atom, which substituent $R_2$, when $n$ is 2 or 3, may be the same or different,
 $p$: an integer from 0 to 3,
 Y: a substituent which, when $p$ is 2 or 3, may be the same or different.

The symbol Y in the above formula may preferably be $NO_2$, a halogen atom, OH, $CF_3$, an alkyl group, an alkoxy group, COOH or a COO-alkyl group.

The term "alky" as used herein, refers to a straight or branched chain saturated aliphatic hydrocarbon group having one to six carbon atoms, such as methyl, ethyl, propyl, isopropyl, n-butyl, t-butyl, pentyl or hexyl. The alkyl in the mentioned alkoxy groups have the same significance.

Preferred compounds of the present invention are compounds of the general formula (I) in which the symbols are as follows:
 A: a hydrogen atom,
 B: an alkoxy group, preferably a methoxy or ethoxy group, or,
 A B: when taken together, a further single bond between the adjacent carbon atoms, or an oxygen atom,
 C: a hydrogen atom,
 D: a hydrogen atom, or,
 C D: when taken together, a further single bond between the adjacent carbon atoms,
 R: a methyl or ethyl group,
 $R_1$: a methyl or ethyl group,
 $n$: an integer which is 1 or 2,
 $R_2$: a hydrogen atom or a methyl group, which substituent $R_2$ when $n$ is 2, may be the same or different,
 $p$: an integer which is 0, 1 or 2,
 Y: an alkyl group, preferably a methyl or ethyl group, or a halogen atom, which substituent Y, when $p$ is 2, may be the same or different. Preferably, the pyridyl unit, whether $p$ is 0, 1 or 2, is connected to the rest of the molecule as a 2-pyridyl group.

The compounds of the general formula (I) may be prepared, for example, by the following processes:
 a. By etherformation (O-alkylation) between a compound of the general formula (II) and a compound of the general formula (III),

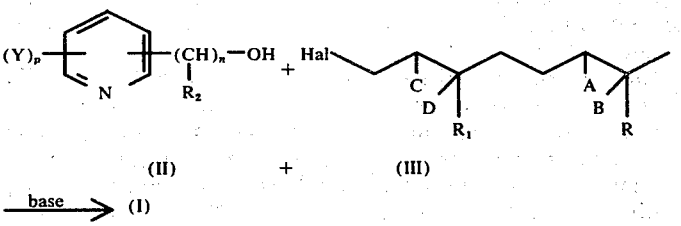

$$\xrightarrow{\text{base}} (I)$$

wherein the symbols A, B, C, D, R, $R_1$, $R_2$, $n$, $p$, and Y have the same meaning as mentioned above and Hal is chlorine, bromine or iodine.

b. By epoxydation of a compound of the general formula (IIIa) to form a compound of the general formula (IIIb) followed by an etherformation according to process (a) to form a compound of the general formula (Ia),

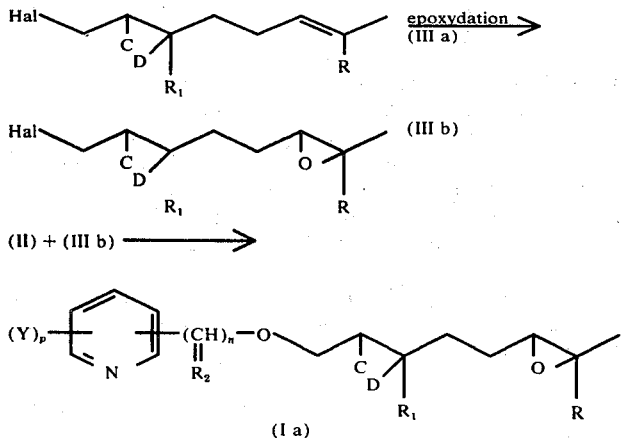

c. By alkoxylation of a compound of the general formula (IIIa) to form a compound of the general formula (IIIc), followed by an etherformation according to process (a) to form a compound of the general formula (Ib),

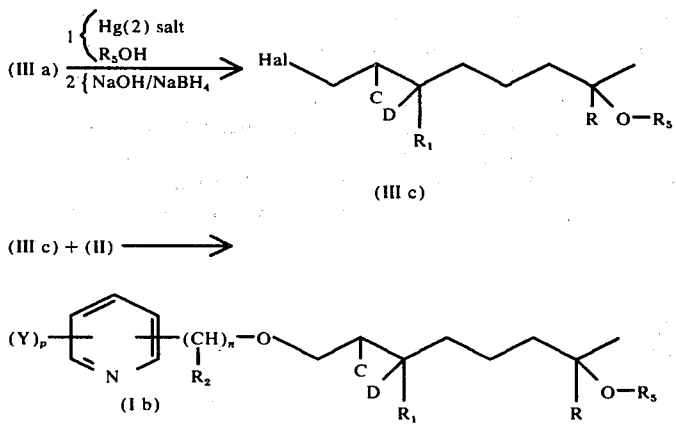

wherein $R_5$ is an alkyl group with from 1 to 6 carbon atoms.

The reaction according to process (a) between a compound of the general formula (III) and a compound of the general formula (II) is preferably performed in the presence of a base, especially sodium hydride or potassium hydroxide, in an organic aprotic solvent, especially dimethylformamide (DMF) or dimethoxy ethane.

The compounds of the general formula (I) can, for example, be prepared according to this process from a chloride, bromide or iodide of the general formula (III) by reacting it with a 10% molar excess of the appropriate compound of the general formula (II) and sodium hydride or powdered potassium hydroxide in DMF or dimethoxy ethane. The reaction mixture is stirred for 3 to 20 hours at a temperature between 20° and 60° C, then diluted with water and extracted with ethyl ether. The organic extract is washed with a 10% KOH solution and finally with water. The extract is then dried over anhydrous $Na_2SO_4$, and the solvent is removed in vacuo. The resulting crude compound of the general formula (I) is purified by column chromatography on silica gel, using a benzene/ethylacetate mixture for the elution.

The purity can be established to 99% by GLC and HPLC and combined spectrometric methods.

The epoxydation process according to (b) is performed with 3-chloroperbenzoic acid as the epoxydizing agent.

The compounds of the general formula (IIIa) can, for example, be epoxydized by reaction with 3-chloroperbenzoic acid in dichloromethane at 0° to 5° C for two hours. A 10% molar excess of the peracid is used. After the epoxidation is completed, the reaction mixture is poured into an ice-cold 10% $NaHCO_3$ solution and is shaken thoroughly. The organic layer is then washed with water, dried over anhydrous $Na_2SO_4$, and the solvent is removed in vacuo.

The epoxy halogenide of the general formula (IIIb) thus formed is reacted with a compound of the general formula (II) according to process (a) as described above, to form a compound of the general formula (Ia).

In process (c), the terminally alkoxylated compounds of the general formula (Ib) can be prepared by the oxymercuration procedure of Brown, H. C., et al.: J. Am. Chem. Soc., 91, 5646, (1969).

The alkenes of the general formula (IIIa) are, for example, treated with mercuric acetate in the appropriate alcohol, i.e. the alcohol of the formula $R_5OH$, resulting in the desired alkoxy group in the end product, and the resulting oxymercury intermediate is reduced by adding aqueous 3 M NaOH and 0.5 M $NaBH_4$ in 3 M NaOH. The mixture is stirred for two hours, until the mercury has coagulated and settled. The reaction product is extracted with n-hexane, the extract washed with water, dried over anhydrous $Na_2SO_4$, and the solvent removed in vacuo. The resulting alkoxylated halogenides of the general formula (IIIc) are reacted with compounds of the general formula (II) according to process (a) to form the terminally alkoxylated compounds of the general formula (Ib).

The starting materials, compounds of the general formula (II), may be made by standard methods from the appropriate substituted pyridines. Kost, A. N., Terent'ev, P. B. and Golovleva, L. A., Vestn. Mosk. Univ., Ser. II, Khim. 19, 56 (1964), C. A., 62 9100 (1965).

The starting materials of the general formula (III), may, for example, be either geranylbromide or -chloride, or citronellychloride or -bromide, and may be made by standard methods.

All chemical structures are confirmed by a combination of infrared and nuclear magnetic resonance (IR and NMR) data.

In accordance with the present invention, there is provided a method for the control of insects, which comprises bringing the insects, or their eggs or larvae into contact with a compound selected from those of the general formula (I) in an amount effective to inhibit the metamorphosis of said insect or to act as sterilizing or ovicidal agent.

Said compounds have been found to act on species of different orders all over the class of insects, viz. Coleoptera (beetles, weevils), Lepidoptera (butterflies, moth), Hemiptera (bugs, plant lice, scales), Orthoptera (grass hoppers), Dictyoptera (roaches), and Diptera (flies, mosquitos).

Accordingly, the invention also includes a composition containing a compound of the general formula (I), which composition is suitable for the control of insect pests. To achieve a uniform distribution or application, it is advantageous to employ a composition comprising an inert carrier and, as the essential active ingredient, a compound of the general formula (I).

One method for the control of insects in accordance with the present invention is to apply the composition comprising an inert carrier and a compound of the general formula (I) to the locus of insect infestation, such as to the vegetation on which the insects live. These compositions can be either solid or liquid.

Solid compositions for treating insects can be prepared by incorporating the active ingredient in an inert carrier such as finely divided talc, silica pyrophyllite, diatomite or clay or granular inert carriers, such as the vermiculites.

Liquid compositions can be prepared by mixing the active ingredient with carriers, such as acetone, xylene, peanut oil, cotton-seed oil, sesame oil and other vegetable oils and mineral oils conventionally employed as carriers in insecticidal formulations for application by spraying. Emulsions containing the active ingredient can also be used.

Other ingredients can be present in the composition of the present invention to aid in the effective application of the active ingredient, such as wetting agents, dispersing agents, insect attractants and the like.

The concentration of active ingredient of a compound of the general formula (I) in the composition can vary depending on a variety of factors, such as the specific insect involved, the degree of insect infestation, environment and weather conditions, and the type of application device used.

Generally, the composition will contain less than 95% by weight of the active ingredient and more frequently less than 10% by weight.

The compounds of the general formula (I) are useful insect control agents by virtue of their ability to inhibit the metamorphosis of said insect. The expression "to inhibit the metamorphosis of said insect" as used herein, and in the appending claims, is used to describe the direct effect of the compounds of the general formula (I) as well as the indirect insecticidal effect of said compounds.

The compounds of the general formula (I) inhibit metamorphosis of various insect species at different stages, resulting in non-viable intermediates. Depending on the time of application, the compounds of the general formula (I) show ovicidal, larvicidal or pupicidal effect. When applied to the adult insect, the effect is indirect in the sense that the insect produces non-viable eggs.

The following examples are presented to further illustrate the present invention, without limiting it to the specific compounds mentioned here.

EXAMPLE NO. 1

Etherformation

Preparation of 3,7-dimethyl-2,6-octadien-1-yl-(2-pyridyl) methylether.

To a mixture of 18.6 g. (0.20 moles) 2-hydroxymethylpyridine in dry DMF is added, in small portions, 8.8 g. of sodium hydride (60% in oil), and the mixture is stirred for one hour at 60° C. Then 34.6 g. (0.2 moles) geranylchloride is added and the reaction mixture is stirred overnight at 50°–60° C. 200 ml. of water is added to the reaction mixture, which then is extracted with ethyl ether. After separation the organic layer is washed with a 10% KOH solution and then with water until neutral. The extract is dried over anhydrous $Na_2SO_4$, and the solvent is removed in vacuo. The yield was 36.5 g. of the crude ether, which was purified on silica gel as described below. The actual compound have $n_D^{24}$: 1.5048.

EXAMPLE NO. 2

Epoxydation

Preparation of 6,7-epoxy-3,7-dimethyl-2-octen-1-yl-(5-ethyl-2-pyridyl)methylether.

To a stirred, chilled (0° C) solution of 3.4 g. geranylchloride in 100 ml. dichloromethane is cautiously added 4.5 g. (0.022 moles) 85% 3-chloroperbenzoic acid in 30 ml. dichloromethane. The reaction mixture is stirred in an ice-bath for 2 hours, then 10% aqueous $NaHCO_3$ solution is added and the mixture shaken thoroughly. The aqueous layer is extracted with dichloromethane and the combined extracts are evaporated in vacuo. The residue is dissolved in ethyl ether, washed twice with 10% $NaHCO_3$ solution and finally twice with water. The etheral extract is dried over anhydrous $Na_2SO_4$ and evaporated in vacuo. 1.9 g. (0.01 moles) of crude 6,7-epoxygeranylchloride thus obtained is poured into a solution of 1.2 g. (0.01 moles) 5-ethyl-2-hydroxymethylpyridine in 20 ml. DMF and 0.44 g. (0.011 moles) sodiumhydride according to the etherformation described above. For the actual compound was found $n_D^{24}$: 1.5013.

EXAMPLE NO. 3

Alkoxylation

Preparation of 7-ethoxy-3,7-dimethyl-2-octen-1-yl-(5-ethyl-2-pyridyl)methylether.

3.4 g. geranylchloride (0.02 moles) is added to a vigorously stirred suspension of 6.4 g. mercuric acetate in 30 ml. of 99% ethanol at 0° C. One hour after the addition of the diene, the mercurial intermediate is reduced by adding 20 ml. 0.5 M $NaBH_4$ in 3 M NaOH. The mixture is stirred for two hours, until the mercury has coagulated and settled. Then the product is extracted with n-hexane and the solvent removed in vacuo. 1.1 g. (0.005 moles) of crude 7-ethoxygeranylchloride thus obtained is reacted with 0.6 g. (0.005 moles) 5-ethyl-2-hydroxymethylpyridine in 5 ml. DMF and 0.22 g. (0.0055 moles) sodiumhydride, according to the etherformation described above. For the actual ether was found $n_D^{24}$: 1.4850.

EXAMPLE NO. 4

Preparation of 5-ethyl-2-hydroxymethylpyridine.

60 g. 5-ethyl-2-methylpyridine was treated 12 hours at 70°–80° C with 85 ml. of 33% $H_2O_2$ in 300 ml. acetic acid. The N-oxide thus obtained was refluxed in acetic acid anhydride and the resulting 2-acetoxymethyl-5-ethylpyridine was hydrolyzed by refluxing it with 50 ml. 10% NaOH in 20 ml. $CH_3OH$. The overall yield of 5-ethyl-2-hydroxymethylpyridine was, without isolation of the intermediates, 83%. The product had a boiling point at 144° C at 18 torr. and we found $n_D^{24}$: 1.5520.

NMR spectra were recorded at 60 Mc/s on a Varian α-60 spectrometer with TMS as internal reference standard (δ units).

EXAMPLE NO. 1

NMR spectra (in $CCl_4$) displayed the following peaks:
8.40 ppm multiplet. (6-H in the pyridine nucleus)
7.75 – 6.90 ppm multiplet. (3-H, 4-H and 5-H in the pyridine nucleus)
5.31 ppm triplet. Broad. (2-H)
5.02 ppm Broad. (7-H)
4.48 ppm singlet. (—O—$CH_2$-pyridine)
3.99 ppm doublet. (1-$H_2$)
2.2 – 1.7 ppm multiplet. (4-H and 5-H)
1.62 ppm singlet. (8-$H_3$, 7-$CH_3$)
1.55 ppm singlet. (3-$CH_3$)

EXAMPLE NO. 2

NMR spectra (in $CCl_4$) displayed the following peaks:
8.30 ppm multiplet. (6-H in the pyridine nucleus)
7.38 ppm multiplet. (2-H and 3-H in the pyridine nucleus)
5.41 ppm triplet. Broad. (2-H)
4.50 ppm singlet. (—O—$CH_2$-pyridine)
4.05 ppm doublet. (1-$H_2$)
2.63 ppm quartet. ($CH_3$—$CH_2$-pyridine
2.56 ppm triplet. (6-H)
2.3 – 1.3 ppm multiplet. (4-$H_2$ and 5-$H_2$)
1.66 ppm singlet. (3-$CH_3$)
1.23 ppm singlet. (8-$H_3$, 7-$CH_3$)
1.20 ppm triplet. ($CH_3$—$CH_2$-pyridine)

EXAMPLE NO. 3

NMR spectra (in $CCl_4$) displayed the following peaks:
8.25 ppm multiplet. (6-H in the pyridine nucleus)
7.35 ppm multiplet. (2-H and 3-H in the pyridine nucleus)
5.35 ppm triplet. (2-H)
4.47 ppm singlet. (—O—$CH_2$-pyridine
4.01 ppm doublet. (1-$H_2$)
3.28 ppm quartet. (—O—$CH_2$-$CH_3$)
2.62 ppm quartet. ($CH_3$—$CH_2$-pyridine)
2.1 – 1.3 ppm multiplet. (4-$H_2$, 5-$H_2$ and 6-$H_2$)
1.64 ppm singlet. (3-$CH_3$)
1.30 ppm triplet. ($CH_3$—$CH_2$-pyridine)
1.07 ppm triplet. ($CH_3$—$CH_2$—O—)
1.07 ppm singlet. (8-H, 7-H)

EXAMPLE NO. 4

NMR spectra (in $(CD_3)_2SO$) displayed the following peaks:
9.62 ppm Broad. (OH)
8.15 ppm multiplet. (6-H in the pyridine nucleus)
7.11 ppm multiplet. (2-H and 3-H in the pyridine nucleus)
4.35 ppm quartet. (—$CH_2$— in the ethyl group)
1.20 ppm triplet. (—$CH_3$ in the ethyl group)

EXAMPLE NO. 5

Chromatography 10 g. crude 3,7-dimethyl-2,6-octadien-1-yl-(2-pyridyl)-methylether is purified by column chromatography on silica gel (0,063 –0,1 mm.). The column is filled with 250 g. silica gel and a benzene/ethylacetate mixture (9/1 by volume). The elution is done with a 9/1 mixture of benzene/ethylacetate. 1000 ml. was used in the elution. The same procedure was applied to all other compounds.

EXAMPLE NO. 6

Formulation

The active ingredient prepared according to example No. 1 can be formulated in the following way:
Active ingredient: 10.0 g.
70% Ca-dodecylphenylsulfonate: 5.0 g.
Oleyl-poly(15)ethyleneoxidether: 5.0 g.
Acetone: ad 100 ml. (100 g/l a.i.)

When poured into water, an emulsion is immediately formed, which shortly after transforms into a transparent solution. Further dilution to any desired concentration can be performed.

The water-based solution is ready for spraying.

In accordance with the examples given above, the following compounds of table No. 1 have been prepared.

Table No. 1

| Comp. No. | Formula and name. | $n_D^{24}$ |
|---|---|---|
|  | 3,7-dimethyl-2,6-octadien-1-yl-(2-pyridyl)methylether |  |

Table No. 1-continued

| Comp. No. | Formula and name | $n_D^{24}$ |
|---|---|---|
| 1. | 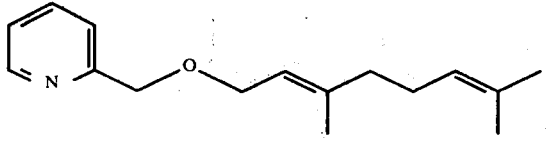 3,7-dimethyl-2,6-octadien-1-yl-(3-pyridyl)methylether. | 1.5048 |
| 2. | 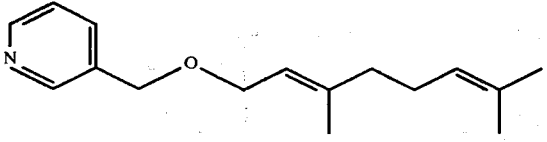 3,7-dimethyl-2,6-octadien-1-yl-(4-pyridyl)methylether. | 1.5088 |
| 3. | 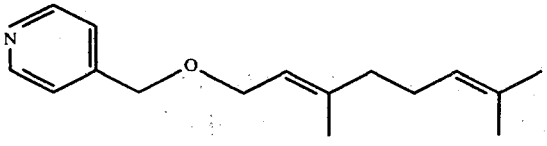 6,7-epoxy-3,7-dimethyl-2-octen-1-yl-(2-pyridyl)methylether. | 1.4689 |
| 4. | 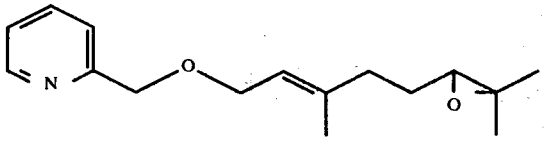 3,7-dimethyl-2,6-octadien-1-yl-(5-ethyl-2-pyridyl)methylether. | 1.5131 |
| 5. | 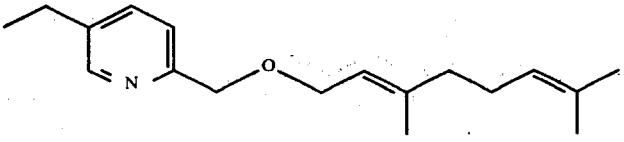 6,7-epoxy-3,7-dimethyl-2-octen-1-yl-(5-ethyl-2-pyridyl)methylether. | 1.5180 |
| 6. | 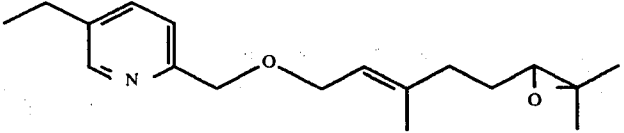 3,7-dimethyl-2,6-octadien-1-yl-1-(2-pyridyl)-1-ethylether. | 1.5013 |
| 7. | 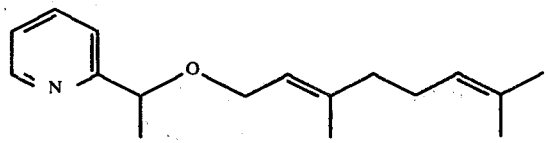 3,7-dimethyl-2,6-octadien-1-yl-(6-methyl-2-pyridyl)methylether. | 1.5033 |
| 8. | 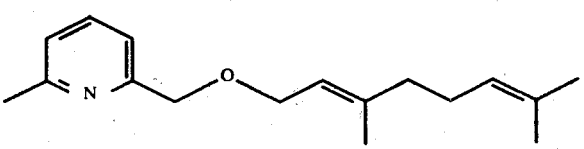 3,7-dimethyl-2,6-octadien-1-yl-2-(2-pyridyl)-1 ethylether. | 1.5099 |

Table No. 1-continued

| Comp. No. | Formula and name. | $n_D^{24}$ |
|---|---|---|
| 9. | 7-ethoxy-3,7-dimethyl-2-octen-1-yl-(5-ethyl-2-pyridyl)methylether. | 1.5028 |
| 10. | 3,7-dimethyl-2,6-octadien-1-yl-(4,6-dimethyl-2-pyridyl)methylether. | 1.4850 |
| 11. | 3,7-dimethyl-6-octen-1-yl-(2-pyridyl)methylether. | 1.5050 |
| 12. | 3,7-dimethyl-2,6-octadien-1-yl-(5-methyl-2-pyridyl)methylether. | 1.4867 |
| 13. | 3,7-dimethyl-2,6-octadien-1-yl-(6-chloro-2-pyridyl)methylether. | 1.5080 |
| 14. | 3,7-dimethyl-2,6-octadien-1-yl-(4-methyl-2-pyridyl)methylether. | 1.5113 |
| 15. | 3,7-dimethyl-6-octen-1-yl-(5-ethyl-2-pyridyl)methylether. | 1.5087 |
| 16. | 6,7-epoxy-3,7-dimethyl-oct-1-yl-(5-ethyl-2-pyridyl)methylether. | 1.4838 |

Table No. 1-continued

| Comp. No. | Formula and name. | $n_D^{24}$ |
|---|---|---|
| 17. | 7-ethoxy-3,7-dimethyl-oct-1-yl-(5-ethyl-2-pyridyl)methylether. | 1.4799 |
| 18. | 7-methoxy-3,7-dimethyl-2-octen-1-yl-(5-ethyl-2-pyridyl)methylether. | 1.4875 |
| 19. | 3-ethyl-7-methyl-2,6-nonadien-1-yl-(5-ethyl-2-pyridyl)methylether. | 1.4871 |
| 20. | 6,7-epoxy-3-ethyl-7-methyl-2-nonen-1-yl-(5-ethyl-2-pyridyl)methylether. | 1.5120 |
| 21. | 7-ethoxy-3-ethyl-7-methyl-2-nonen-1-yl-(5-ethyl-2-pyridyl)methylether. | 1.4962 |
| 22. | | 1.4825 |

TESTING FOR JUVENILE HORMONE ACTIVITY.

The biological tests are examplified by tests on *Tenebrio molitor* L, *Galleria mellonella* L. and *Culex pipiens* L.

*Tenebrio* test:

The material in question is applied topically to the abdomen of 0.5 to 2 hours old pupae of the said species, as a solution in acetone. The pupae are held at 27° C and 70% RH, ecdysis occuring 5 to 7 days layer. The degree of inhibition of adult characters is referred to an arbitrary scale, where a morphologically perfect adult is given the character 0%, and a perfect second pupae 100%.

Galleria test:

The test is performed on eggs deposited on impregnated filter paper by the mother moth. The data given in table 2, are the amount necessary for preventing eclosion of 50% of the eggs. The amount (IC-50 eclos.) is given in mg./65 cm².

Culex test:

The compounds are tested on mature larvae. The concentration necessary to produce a loss of 50% of the test animals is given in table 2. The concentration (IC-50 eclos.) is given in ppm.

Table No. 2.

| Compound No. | Tenebrio test ID-50 morph. µg/pupa | Galleria test IC-50 eclos. mg/65 cm² | Culex test IC-50 eclos. ppm |
| --- | --- | --- | --- |
| 1. | 1 | 10 | 5 |
| 2. | 40 | 10 | 3 |
| 3. | >100 | 6 | >10 |
| 4. | 0.3 | >10 | 9 |
| 5. | 0.05 | 10 | 0.3 |
| 6. | 0.04 | >10 | 0.005 |
| 7. | 4 | 10 | 10 |
| 8. | 4 | >10 | 10 |
| 9. | 3 | >10 | 10 |
| 10. | 0.03 | 10 | — |
| 11. | 100 | >10 | — |
| 12. | 0.9 | 2 | 1 |
| 13. | 0.5 | 1 | — |
| 14. | >100 | >10 | — |
| 15. | 5 | 10 | — |
| 16. | 0.1 | 10 | 0.1 |
| 17. | 0.3 | — | 0.01 |
| 18. | 0.1 | 10 | — |
| 19. | 0.5 | — | — |
| 20. | 0.01 | 1 | 0.05 |
| 21. | 0.008 | <1 | 0.005 |
| 22. | 0.01 | 5 | — |

All compounds tested are mixtures of isomers.

What we claim is:

1. A novel chemical compound of the general formula (I):

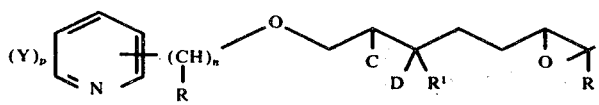

wherein
C is hydrogen,
D is hydrogen,
C and D when taken together form a further single bond between the adjacent carbon atoms,
R is methyl or ethyl,
R₁ is methyl or ethyl
n is an integer from 1 to 3,
R₂ is alkyl or hydrogen and when n is 2 or 3 may be the same or different,
p is an integer from 0 to 3 and
Y is NO₂, halogen, OH, CF₃, alkyl, alkoxy, COOH or COOalkyl and when p is 2 or 3 or may be the same or different.

2. A compound as claimed in claim 1, in which the symbols in formula (I) are as follows:
    n: an integer which is one or two,
    R₂: a hydrogen atom or an alkyl group, which substituent R₂, when n is 2, may be the same or different,
    p: an integer which is zero, one or two,
    Y: an alkyl group, or a halogen atom, which substituent Y, when p is 2, may be the same or different.

3. A compound as claimed in claim 1 in which the symbols are as follows:
    n: an integer which is one or two,
    R₂: a hydrogen atom or a methyl group, which substituent R₂, when n is two, may be the same or different,
    p: an integer which is zero, one or two,
    Y: a methyl or ethyl group or a halogen atom, which substituent Y, when p is two, may be the same or different.

4. A compound as claimed in claim 1, in which the pyridyl unit, whether p is zero, one or two, is connected to the rest of the molecular as a 2-pyridyl group.

5. A compound as claimed in claim 1, in which the symbol R₂ represents a hydrogen atom.

6. A compound as claimed in claim 1, which is 6,7-epoxy-3,7-dimethyl-2-octen-1-yl-(2-pyridyl)methyl ether.

7. A compound as claimed in claim 1, which is 6,7-epoxy-3,7-dimethyl-2-octen-1-yl-(5-ethyl-2-pyridyl)-methyl ether.

8. A compound as claimed in claim 1, which is 6,7-epoxy-3,7-dimethyl-oct-1-yl-(5-ethyl-2-pyridyl)methyl ether.

9. A compound as claimed in claim 1, which is 6,7-epoxy-3-ethyl-7-methyl-2-nonen-1-yl-(5-ethyl-2-pyridyl)methyl ether.

* * * * *